(12) United States Patent
Soltz et al.

(10) Patent No.: US 9,006,182 B2
(45) Date of Patent: *Apr. 14, 2015

(54) LIGHT ACTIVATED COMPOSITE TISSUE ADHESIVES

(75) Inventors: Barbara A. Soltz, Spring Valley, NY (US); Robert Soltz, Spring Valley, NY (US)

(73) Assignee: Conversion Energy Enterprises, Inc., Spring Valley, NY (US)

( * ) Notice: Subject to any disclaimer, the term of this patent is extended or adjusted under 35 U.S.C. 154(b) by 623 days.

This patent is subject to a terminal disclaimer.

(21) Appl. No.: 12/943,763

(22) Filed: Nov. 10, 2010

(65) Prior Publication Data

US 2011/0125187 A1   May 26, 2011

(51) Int. Cl.
| | |
|---|---|
| A61K 38/39 | (2006.01) |
| A61K 47/48 | (2006.01) |
| A61K 38/00 | (2006.01) |
| A61P 43/00 | (2006.01) |
| A61B 17/50 | (2006.01) |
| A61B 17/08 | (2006.01) |
| A61D 1/00 | (2006.01) |
| A61K 38/17 | (2006.01) |
| C07K 1/00 | (2006.01) |
| C07K 14/00 | (2006.01) |
| C07K 16/00 | (2006.01) |
| C09H 1/00 | (2006.01) |
| C07K 17/00 | (2006.01) |
| C08H 1/00 | (2006.01) |
| A61F 13/00 | (2006.01) |
| A61F 2/00 | (2006.01) |
| A61K 9/70 | (2006.01) |
| A61B 17/00 | (2006.01) |
| A61K 31/525 | (2006.01) |
| A61K 47/42 | (2006.01) |
| A61L 31/04 | (2006.01) |
| A61L 31/14 | (2006.01) |

(52) U.S. Cl.
CPC ..... *A61B 17/00491* (2013.01); *A61B 2017/005* (2013.01); *A61K 9/7007* (2013.01); *A61K 31/525* (2013.01); *A61K 38/39* (2013.01); *A61K 47/42* (2013.01); *A61L 31/044* (2013.01); *A61L 31/14* (2013.01)

(58) Field of Classification Search
None
See application file for complete search history.

(56) References Cited

U.S. PATENT DOCUMENTS

| | | | | | |
|---|---|---|---|---|---|
| 5,552,452 | A | * | 9/1996 | Khadem et al. | 522/63 |
| 5,837,747 | A | * | 11/1998 | Soon-Shiong et al. | 522/26 |
| 6,183,498 | B1 | | 2/2001 | Devore et al. | |
| 6,773,699 | B1 | | 8/2004 | Soltz et al. | |
| 6,875,427 | B1 | * | 4/2005 | DeVore et al. | 424/78.03 |
| 6,939,364 | B1 | * | 9/2005 | Soltz et al. | 606/214 |
| 2002/0006394 | A1 | * | 1/2002 | Redmond et al. | 424/93.7 |
| 2010/0028407 | A1 | * | 2/2010 | Del Priore et al. | 424/443 |
| 2011/0125187 | A1 | | 5/2011 | Soltz et al. | |
| 2013/0035629 | A1 | * | 2/2013 | Soltz et al. | 604/20 |

OTHER PUBLICATIONS

U.S. Appl. No. 13/943,771, filed Nov. 2010, Soltz et al.*
David Brett, A Review of Collagen and Collagen-based Wound Dressing, Wounds 2008; 20(12).
Hardwick et al., Separation, Identification and Quantification of Riboflavin and its Photoproducts in Blood Products using High-performance Liquid Chromatography with Fluorescence Detection: A Method to Support Pathogen Reduction Technology, Photochem. and Photbiol., 80(3) pp. 609-615 (2004).
Ibusuki et al;, Photochemically Cross-Linked Collagen Gels as Three-Dimensional Scaffolds for Tissue Engineering, Tissue Engineering, 13(8) 1995-2001 (2007).
Wollensak et al., Riboflavin/Ultraviolet-A-induced Collagen Crosslinking for the Treatment of Kertoconus, Am. J. Ophthalmol, 2003; 135:620-627.

* cited by examiner

*Primary Examiner* — James H Alstrum Acevedo
*Assistant Examiner* — Thea D'Ambrosio

(57) ABSTRACT

A light activated collagen-flavin composite layer incorporating riboflavin is applied as treatment for infected lesions. These composites have also been found to be strong tissue adheives that are effective in closing and sealing wounds, fixation of grafts/ implants and anastomoses. Advantages include speed of closure, reduced infection due to the elimination of foreign matter, evidence of accelerated wound healing and the ease of use in complex surgery, especially when watertight seals, limited access or small repair size are important factors. The riboflavin in the collagen layer is exposed to light (e.g., light having a wavelength between 360-375 nm or 440-480 nm), decomposing the riboflavin to form reactive oxygen species (ROS). Strong crosslinks between the collagen composite and tissue results. In addition, similar exposures eradicate pathogens in the wound.

30 Claims, 15 Drawing Sheets

Table 1

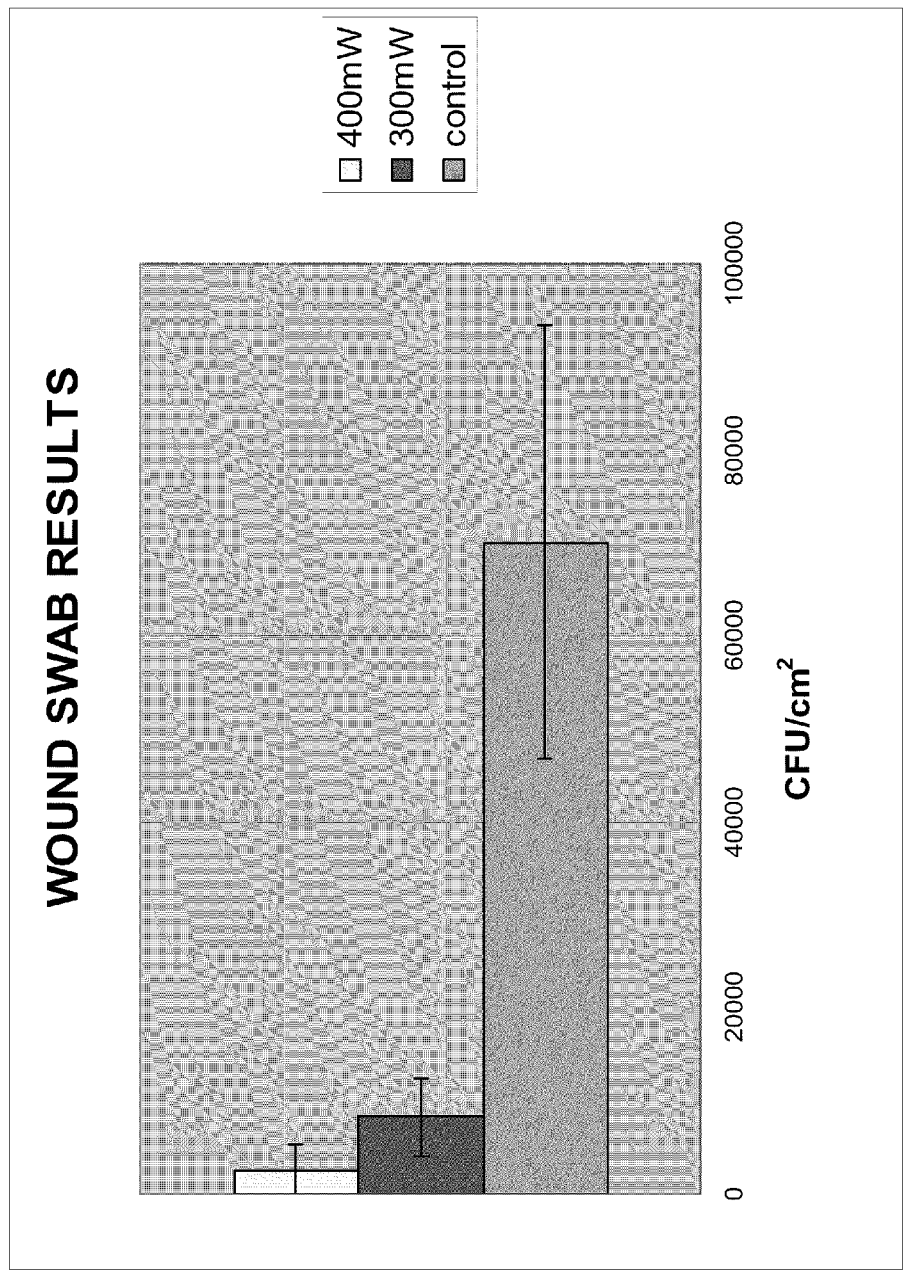

LIGHT ACTIVATED COMPOSITE TISSUE ADHESIVES

The present application claims the benefit of U.S. Provisional Patent Application No. 61/280,925, filed Nov. 10, 2009, the entire contents of which are incorporated herein by reference.

I. BACKGROUND

There has been heightened interest in developing light activated tissue solders and sealants as a substitute for conventional closure methods such as the fixation of grafts/implants and anastomoses. Advantages include speed of closure, reduced infection due to the elimination of foreign matter, evidence of accelerated wound healing and the ease of use in complex surgery, especially when watertight seals, limited access or small repair size are important factors. Laser activation provides a directed energy source for precise placement of the sealing material and can amplify the crosslinking mechanism for bonding together incisional edges or wound tissue flaps.

Numerous studies have reported the efficacy of light activated materials to join soft tissues. The availability of a variety of laser output powers, wavelengths, which match the optical properties of tissue, as well as the development of protein composites, layered materials and those modified with growth factors, chromophores, or photochemicals have advanced the technology. Applications range from urologic anastomoses, small diameter vascular anastomoses, nerve anastomosis and skin closures.

Photothermal processes modulate the strength of the repair and may reach a precise temperature set by the choice of laser and material composition to obtain protein reconstruction at the glue/tissue interface with minimal damage to peripheral tissue. Some of these glue constructs tend to undergo blood dilution during surgery with mechanical alteration thereby weakening the repair. The stronger adhesives are often brittle, inflexible and not easily adapted to different tissue geometries.

In comparison, photochemical processes involve the breaking of photosensitizer bonds, in the presence of energetic light such as UVA, with the resultant generation of reactive species that catalyze and accelerate the formation of linkages to underlying tissue.

Methods to date have not gained clinical acceptance. The major reasons include the high level of surgeon skill that is required, the strength, toxicity and resorbability of the tissue adhesive, the potential for irreparable laser damage and cost of the laser system.

II. SUMMARY OF THE INVENTION

Consistent with the present disclosure, a UVA or blue light source may be employed to activate redox flavins that are contained within, embedded in or conjugated with chemically modified collagen. In addition to chemically modified collagen, other materials such as polylactic or polyglycolic acid, hyaluronic acid gel and polyethylene glycol (PEG) based polymers may be used to distribute and release the photosensitizer to the bonding site.

The spectrum of riboflavin in water in shows an absorption peak at 375 nm and a similar peak centered at 446 nm as shown in FIG. 1a. Light sources are available in these peak regions to promote efficient riboflavin photo-degradation to generate reactive oxygen species (ROS).

The mechanism for riboflavin photo-degradation with the formation of compounds from riboflavin is shown in FIG. 1b. When riboflavin is irradiated with either UVA or blue light, its sugar moiety is cleaved, forming lumichrome in neutral or acidic pH. Lumiflavin is also formed in basic pH. Lumichrome exhibits a peak absorbance at approximately 430 nm while lumiflavin's peak is 450 nm. Both photoproducts are structurally capable of utilizing $\pi \rightarrow \pi^*$ transitions to form ROS.

Consistent with an aspect of the present invention, a method of sealing and closing tissue and wounds is disclosed which comprises a composition that includes a derivatized collagen layer with incorporated photosensitive chromophores including riboflavin, lumichrome or lumiflavin and placed on the tissue. In another aspect of this invention the collagen composition is reacted with a solution of chromophore. Once the chromophore is uniformly distributed within the collagen composition, the layer or thin film is removed from solution and dried to remove any excess chromophore. Alternatively, the chromophore may include lumichrome or lumiflavin. In addition, the layer or film may be exposed to optical energy or light having a wavelength in a range of 360-375 nm (UVA) or 440-480 nm (blue light). Power densities may range from 0.1 W/cm$^2$ to 2 W/cm$^2$. The derivatized collagen can participate in the sealing and closure of wounds associated with trauma or surgery. ROS may be generated by the photo-degradation of the flavin and may disrupt the three-dimensional structure of collagen fibers found in tissues as well as in the derivatized collagen (flavin carrier) promoting crosslinking between tissue and the glue composite, improving both adhesive and cohesive strength.

Further consistent with an additional aspect of the present invention, is application of a collagen layer to treat infected tissue or a wound which comprises a composition of collagen that includes riboflavin and applying that layer on a surface of the infected tissue or wound. Alternatively, the composition of collagen may include lumichrome or lumiflavin. The invention also includes directing a beam of photoradiation toward the collagen composition that includes riboflavin provided on the surface of the tissue or wound such that the beam exposes the composition to the photoradiation, the photoradiation including light having a wavelength in a range of 360-375 nm or 440-480 nm with power densities ranging from 0.1 W/cm$^2$ to 2 W/cm$^2$.

Consistent with the present disclosure, several benefits may be provided as compared to the methods currently used for supplying reagents to tissues for sealing and bonding including solutions or gels that are applied to the wound area. The derivatized collagen incorporated chromophore layer can be sized to any shape or thickness and conforms to curved, flat or irregular tissue surfaces. The collagen compositions can be varied as well as the concentration of the chromophore to optimize the time release of the photosensitizing agent to the target site. The solubility of the chromophore is enhanced in the process of incorporation within the collagen composition. Other advantages include preventing the chromophore from migrating or diffusing to adjacent healthy tissue. The light is so configured so that it impinges only on the conformal layer. The physiological fluids of the tissue increase the solubility of the collagen layer resulting in the chromophore being released and diffused into the treatment area. The collagen layer may also help to obliterate wound dead spaces, and may be a useful adjunctive measure that could reduce the need for drains. The collagen layer appears to bond to wound collagen and as a result will aid in the apposition of the wound surfaces thus minimizing seroma (fluid) accumulation, which is a potential source of infection as these can be primarily or secondarily contaminated. The collagen layer also provides a moist environment an affect that is known to encourage healing. Light penetration is controlled by selection of wavelength range in order to activate only the released chromophore at the wound site.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the present disclosure and together with the description, serve to explain the principles of the disclosure.

III. BRIEF DESCRIPTION OF THE DRAWINGS

FIGS. 9a-9c illustrate results that evidence anti-microbial properties of compositions consistent with the present disclosure.

IV. DETAILED DESCRIPTION OF THE INVENTION

Figure 1A:
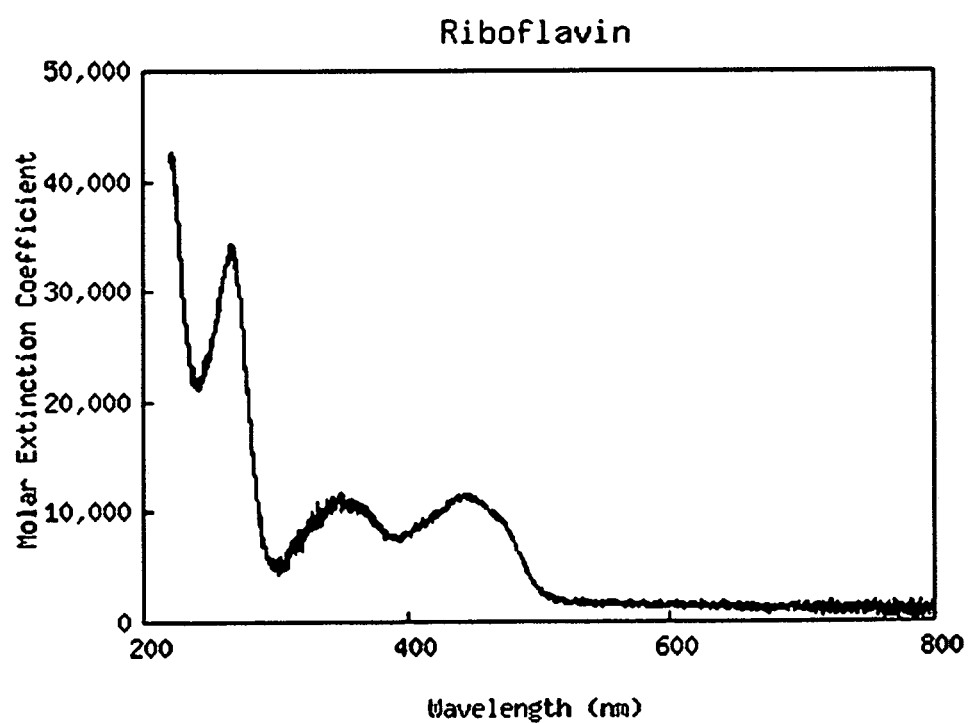
FIG. 1a illustrates riboflavin absorption as a function of wavelength
Figure 1B:
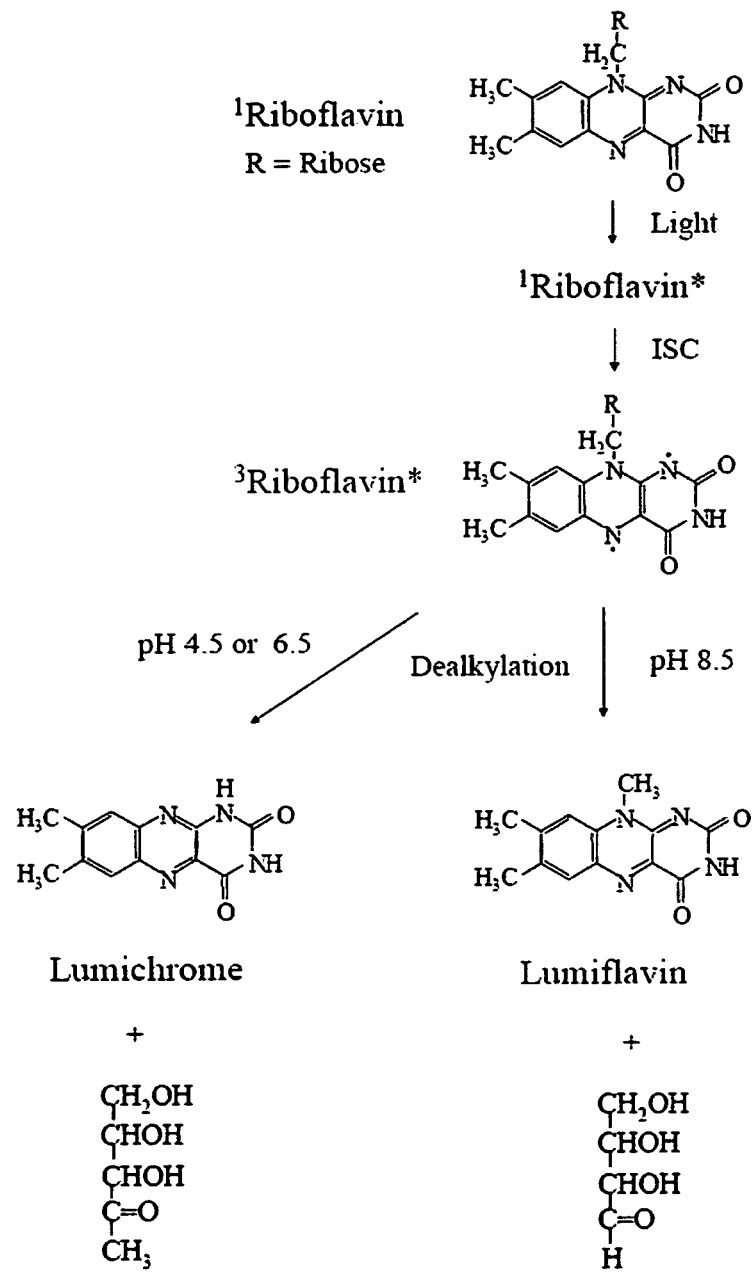
FIG. 1b illustrates the photodecomposition of riboflavin

Reference will now be made in detail to exemplary embodiments of the disclosure, examples of which are illustrated in the accompanying drawings. Wherever possible, the same reference numbers will be used throughout the drawings to refer to the same or like parts.

A layer of collagen that incorporates a photosensitive chromophore such as riboflavin, lumiflavin, lumichrome or a combination of thereof, for example, may be applied directly to a surgical incision or a trauma wound, for example. While the riboflavin diffuses to the affected area, the collagen layer is exposed to light (e.g., light having a wavelength between 360-375 nm or alternatively 440-480 nm) with power densities in the range $0.1 \text{ W/cm}^2$ to $2 \text{ W/cm}^2$. In other examples, the collagen layer may instead contain lumichrome or lumiflavin. A method of preparing a composition consistent with the present disclosure will next be described.

The collagen layer may be made from a collagen which has been extracted, purified, solubilized, chemically modified and reconstituted in accordance with techniques described in U.S. Pat. Nos. 6,773,699 and 6,875,427, the contents of both of which are incorporated herein by reference. Preferably, the starting collagen is prepared from porcine corium, however other sources of collagen may also be used. Porcine hide is rinsed with reagent alcohol to reduce bioburden. The hide is cut into sections approximately 24 inches wide and passed through a "splitter" to remove epidermis and underlying membranous tissue. Split hide is rinsed with reagent alcohol and placed in frozen storage prior to processing. Sections of split corium are cut into small pieces (about 1 $cm^2$) and soaked in reagent alcohol and then washed extensively with sterile water. The chemically disinfected corium is washed extensively in sterile water, weighed and placed in 20 volumes (v/w) of 0.5M acetic acid. The pieces are stirred for 72 hours and porcine mucosal pepsin added to the partially swollen corium.

Pepsin is added at 2% (w/w wet corium) and stirred for 48 hours. At this point, the corium is "dissolved" in acetic acid. Small, undissolved pieces are removed by filtering the thick slurry through cheesecloth. The retained liquid containing collagen is subjected to differential NaCl precipitation to isolate predominantly Type I collagen. Purified Type I collagen at about 5 mg/mL is then dialyzed against 0.1N acetic acid. The retained collagen solution is subsequently filtered through 0.45 µm and 0.2 µm filters. Collagen stock solution is stored at refrigeration temperatures.

Hydroxyproline analysis has determined the pure collagen concentration is 4.88 mg/mL and the UV absorbance profile at 280 nm indicated no presence of pepsin (sensitivity 1 part per billion). SDS-PAGE and Differential Scanning calorimetry (DSC) is conducted to examine the purity of Type I collagen. DSC profiles show transition temperatures of 43° C. indicative of undenatured molecular collagen.

Purified, telopeptide-poor Type I collagen is derivatized with glutaric anhydride. The anhydride reacts with deprotonated free amines and substitutes a carboxyl group ($COO^-$) for the reacted amine group, making the composition anionic. The degree of derivatization is selected so that the modified collagen remains soluble at physiologic pH. Derivatization is performed by adjusting the pH of soluble collagen (5 mg/mL) to 9.0, using NaOH, adding solid anhydride to the collagen at different concentrations ranging from 10%-30% (w/w) solution while maintaining the pH at 9.0 during the reaction. After 15 minutes, the pH of the solution is reduced to about 4.5 to precipitate derivatized collagen. The precipitate is recovered by centrifugation at 14,500 RPM for 20 minutes and 9° C. The precipitate is washed two times with sterile water. The final precipitate is dissolved in 5 mM phosphate buffer at pH 7.2 at a final concentration of 5 mg/mL. The solution is freeze dried in trays at a controlled rate.

Collagen layers are prepared from the lyophilized derivatized collagen. Lyophilized sheets are cut into small pieces and homogenized in a Tekmar Tissue mill. Gelatinized collagen layers are prepared by dissolving collagen powder in sterile phosphate buffer at pH 7.2 and heating the solution to 30-50° C. in a controlled water bath. The collagen solid concentration can range from 10%-65% and is obtained by exposing the dispersions to a controlled temperature water bath. As the collagen dissolves, more powder is added until the desired concentration is achieved (weight to volume). At this step the chromophore may be added as a solid powder to a desired concentration (weight to volume or weight to weight) with continued stirring in a controlled temperature water bath. For example, riboflavin, such as a riboflavin-5-phosphate powder commercially available from Sigma-Aldrich Corporation, may be added to obtain a desired concentration in the collagen, such as a concentration in a range of 0.1% to 2.0% (w/w or w/v) and preferably equal to or substantially equal to a concentration or 1.0% (w/w or w/v). Known powders of lumichrome or lumiflavin may be added to the collagen in a similar manner to achieve a desired concentration of those chromophores, such as a concentration in a range of 0.1% to 2.0% (w/w or w/v) and preferably equal to or substantially equal to a concentration or 1.0% (w/w or w/v). Alternatively, combinations of two or more of lumichrome, lumiflavin, and riboflavin may be added to the collagen in amounts that yield a desired concentration, such as a concentration in a range of 0.1% to 2.0% (w/w or w/v) and preferably equal to or substantially equal to a concentration or 1.0% (w/w or w/v). Once the desired concentration is achieved, the viscous solution may be centrifuged and poured into either round square, or rectangular shaped molds, for example, whereby the height of the mold may be used as a gauge to determine the layer or film thickness. While still warm, a Teflon plate may be pressed onto the filled mold to control layer thickness uniformity. Collagen layer thicknesses may range from 100 μm to 1.5 mm. After cooling for 30 min, the layers may be uniformly colored and transparent and may be removed from the mold, vacuum packaged, sterilized, labeled. They may then be stored at 4° C., for example, until use.

Consistent with a further aspect of the present disclosure, native or gelatinized collagen layers including type I collagen may be prepared as previously described but without the addition of the chromophore, e.g., riboflavin, lumichrome, and/or lumiflavin. Rather, after molding, the collagen layers, which may be clear, may be extracted from the mold and may be weighed. The layers may then be exposed or provided (e.g., dissolved) in a solution in which chromophore is also dissolved. For example, both the chromophore and the collagen (e.g., type I collagen) may be dissolved in a pH 7.2 phosphate buffer solution including distilled water. Alternatively, the collagen and chromophore may be dissolved in an organic solvent including ethanol or chloroform, for example. After 24 hours, or other suitable period of time, the layers may be removed from solution, and excess solvent or water, as the case may be, is preferably removed from the solution, such as by air drying. The layers may then be weighed to determine or confirm the concentration of the chromophore incorporated within the layer (weight to volume or weight to weight).

In one example, riboflavin powder, similar to or the same as the riboflavin powder noted above, may be added to the pH 7.2 phosphate buffer solution including dissolved collagen (e.g., derivatized type I collagen discussed above). The amount of riboflavin may be added to obtain a desired concentration in the collagen, such as a concentration in a range of 0.1% to 2.0% (w/w or w/v) and preferably equal to or substantially equal to a concentration or 1.0% (w/w or w/v). Known powders of lumichrome or lumiflavin may be added to the phosphate buffer in a similar manner to achieve a desired concentration of those chromophores, such as a concentration in a range of 0.1% to 2.0% (w/w or w/v) and preferably equal to or substantially equal to a concentration or 1.0% (w/w or w/v). Alternatively, combinations of two or more of lumichrome, lumiflavin, and riboflavin may be added to the phosphate buffer in amounts that yield a desired concentration, such as a concentration in a range of 0.1% to 2.0% (w/w or w/v) and preferably equal to or substantially equal to a concentration or 1.0% (w/w or w/v).

Figure 2A:
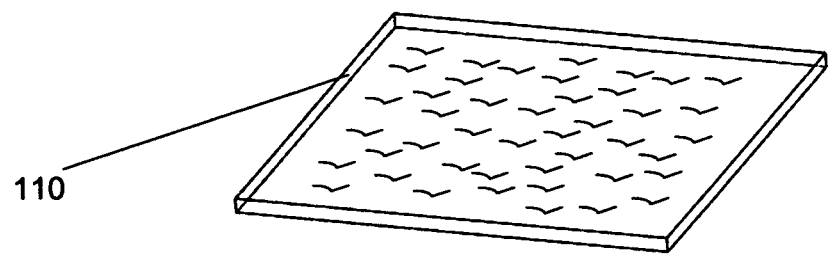
FIGS. 2a and 2b illustrate examples of the collagen layer including the incorporated chromophore.

Fig. 2a shows an exemplary collagen-flavin composite layer 110. Preferably collagen layer 110 is a composition that includes a collagen concentration of 100 mg/ml (10%) up to an including 600 mg/ml (60%). Layer 110 may also include a chromophore that produces a reactive oxygen species upon exposure to electromagnetic radiation, such as ultraviolet light in a range of 360 nm to 375 nm (UVA) or blue light in a range of 440 nm to 480 nm. The concentration of chromophore, eg. riboflavin, lumichrome, or lumiflavin is 0.1 to 2.0% (w/w or w/v) but preferably equal to or substantially equal to 1.0% (w/w or w/v). The collagen may be derivatized with a $COO^-$ functional group, as noted above, and may include combinations of two or more of riboflavin, lumichrome, or lumiflavin. Alternatively, the collagen concentration may be in a range of 300 mg/ml (30%) up to an including 800mg/ml (80%). Further, the collagen may be gelatinized, as further noted above.

Figure 2B:
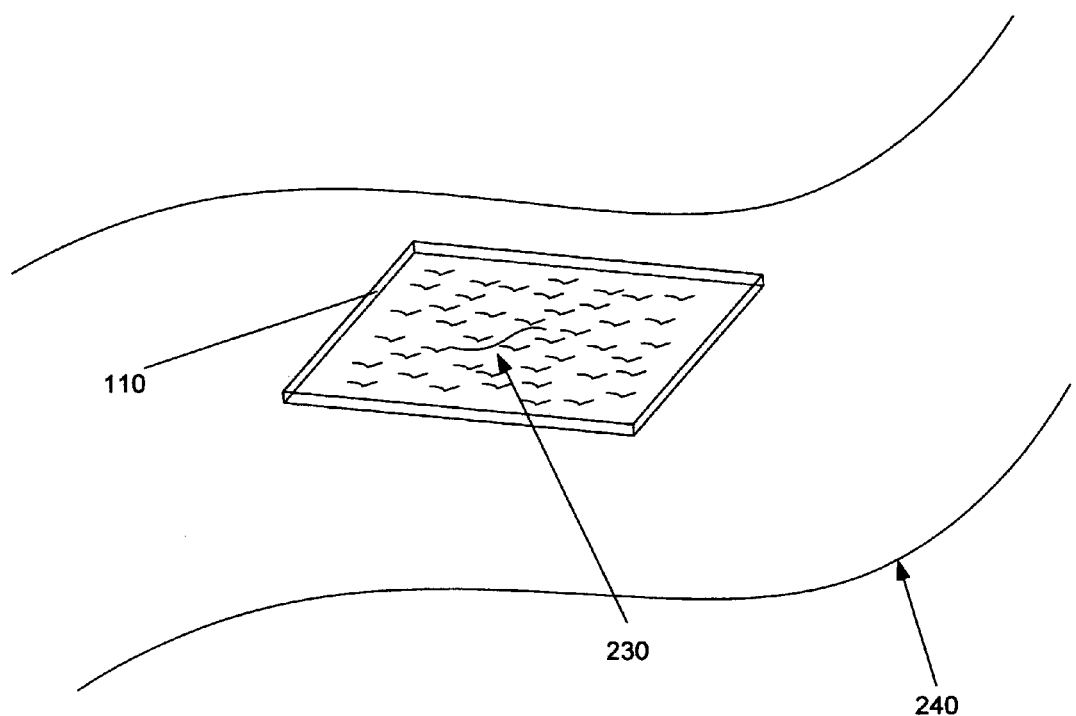

As further shown in Fig. 2b the collagen layer 110 (also referred to as a collagen-flavin composite layer herein), similar to or the same as collagen layer 110 discussed above, may be applied to a human wound 230, such as bacterial-laden lesion or an uncontaminated incisional wound 230 in human tissue 240, for example.

Collagen layer 110 preferably conforms to the surface of the tissue 240 where lesion 230 is located.

Figure 3A:
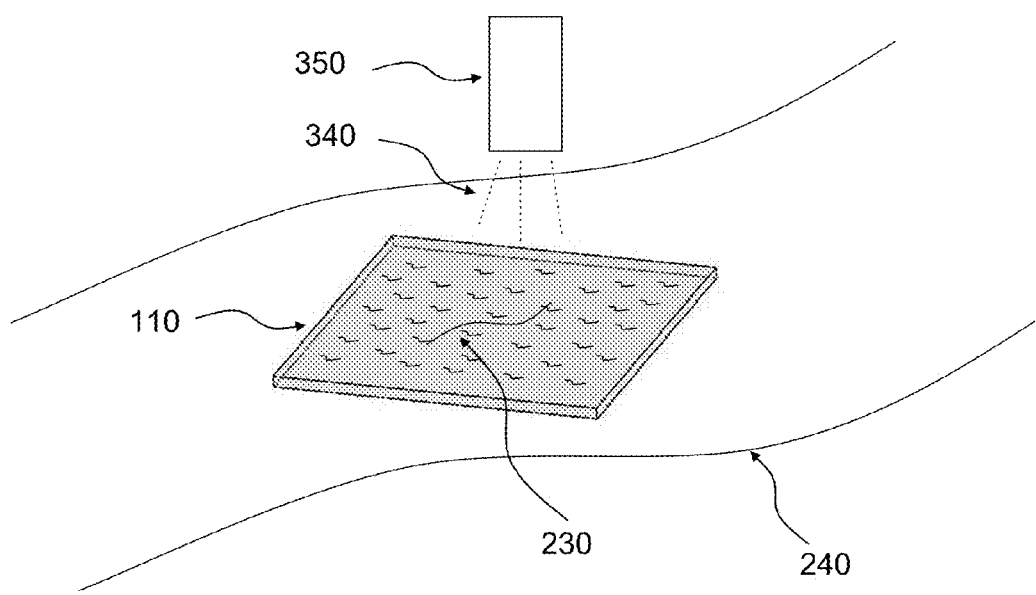
FIG. 3a illustrates exposure of the layer consistent with an additional aspect of the present disclosure.

FIG. 3a shows a first example in which collagen-flavin composite layer 110 is exposed by source 350. Here, source 350 is spaced from and directs optical energy or light 340, typically in a range of 360-375 nm or alternatively 440 to 480 nm towards collagen layer 110 with power densities in the 0.1 $W/cm^2$ to 2 $W/cm^2$, for example. Preferably, light 340 has a wavelength of 450 nm and source 350 may include a filtered white light source, a solid-state laser, a diode laser or light-emitting diodes (LED).

Figure 3B:
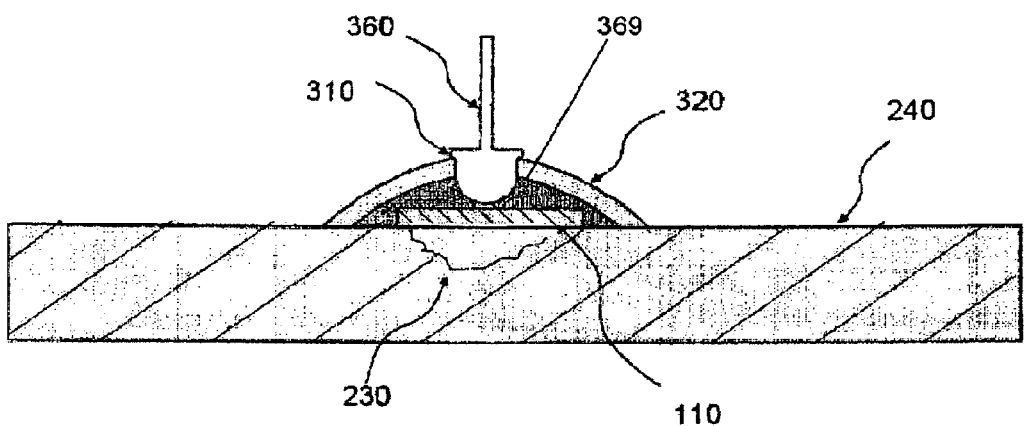
FIG. 3b illustrates exposure of the layer in which the light source is enclosed within an envelope consistent with an additional aspect of the present disclosure.

FIG. 3b shows a second example in which source 360 includes an optical source (supplying light having the wavelengths and power densities noted above, for example), such as LED 310. LED 310 is provided within a shield or envelope 320 in order to direct light to collagen layer 110 provided on wound site or lesion 230 (alternatively the optical source may include a laser diode). In one example, envelope 320 is reflective, such that light from LED 310 reflects off an inner surface of envelope 320 and toward collagen layer 110. Preferably, envelope 320 is provided on human tissue 240 such that envelope 320 covers collagen layer 110 and light source 310 is positioned over lesion or incisional wound 230. Typically, light source 320 is centered over lesion 230. In this example, source 360 may be brought within relatively close proximity to collagen-flavin composite layer 110, so that light may be accurately directed toward the composite layer. Additional benefits of the example shown in FIG. 3b include the reduction in the amount of light power required to expose collagen layer 110 because source 360 may be brought relatively close to collagen layer 110. As a result, more efficient coupling of light power to the wound site or lesion 230 can be achieved. As noted above, a reflective coating 370 may be optionally provided on the internal surface 369 of envelope 320 so that light is reflected toward and supplied more efficiently to collagen-flavin composite layer 110 and is not absorbed by envelope 320. In addition, envelope 320 may have similar dimensions as the composite layer 110 so that light is not supplied to portions of the tissue 240 unaffected by the wound or lesion.

Figure 4:
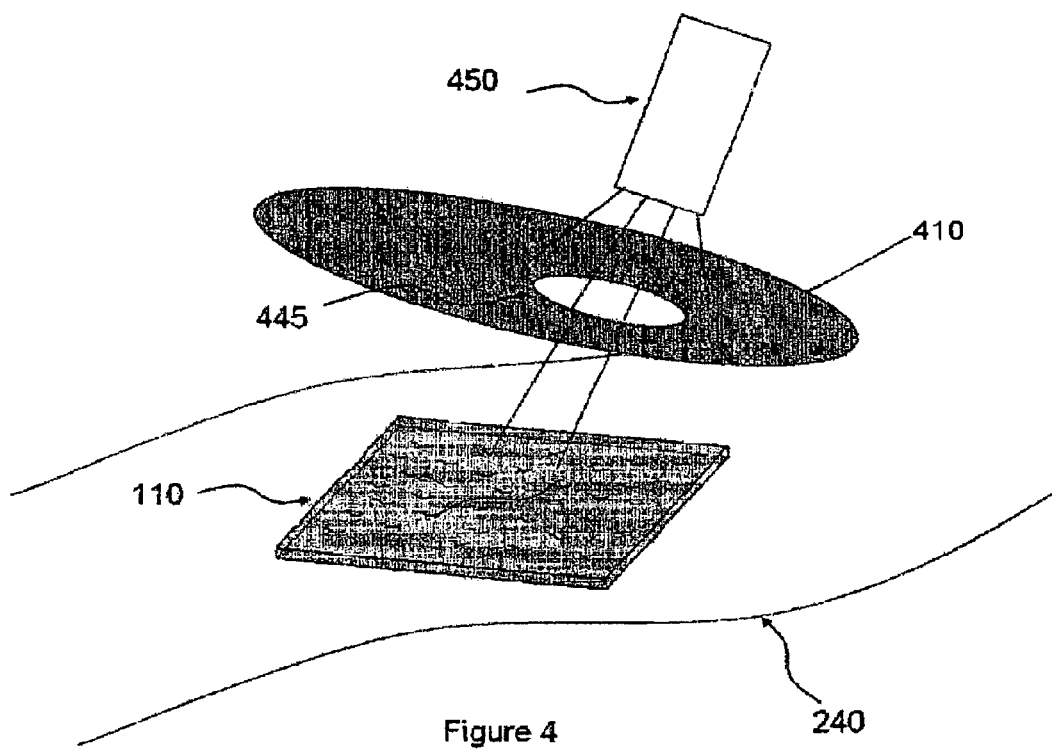
FIG. 4 illustrates exposure of the layer in which the light source passes through an opening in a plate or mask consistent with an additional aspect of the present disclosure.
Figure 5:
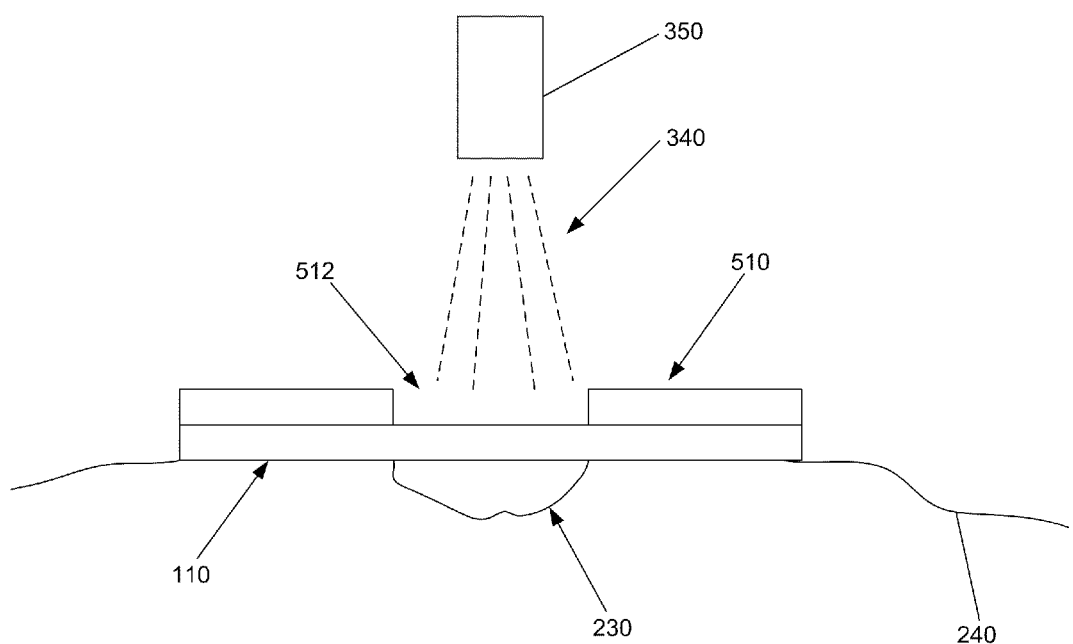
FIG. 5 illustrates exposure of the layer in which the light source passes through an opening in a plate or mask in contact with the layer consistent with an additional aspect of the present disclosure.

FIG. 4 illustrates another example whereby light from source 450 (including an LED, diode laser or solid state laser similar to or the same as that discussed above, for example) passes through an opening 445 in plate or mask 410 and impinges on collagen-flavin composite layer 110. In this example, mask 410 protects healthy portions of tissue 240 from light output from source 450. In addition, although mask 410 is shown spaced from collagen-flavin composite layer 110, it is contemplated that mask 410 may be placed directly in contact with collagen-flavin composite layer 110 or form part of composite layer 110. For example, as shown in FIG. 5, a mask 510 including any suitable material substantially opaque to light in a wavelength range of 360-375 nm or 440 nm to 480 nm be provided on and directly in contact with collagen-flavin composite layer 110, whereby composite layer 110 adheres or sticks to mask 510. Alternatively, collagen-flavin composite layer 110 may be laminated onto mask 510. After exposure, mask 510 may be peeled away or removed, in one example.

As further shown in FIG. 5, light 340 from source 350 may pass through opening 512 in mask 510 to expose a portion of collagen-flavin composite layer 110 overlying lesion or wound 230. In this example, mask 510 may be provided directly on collagen layer 110.

Figure 6:
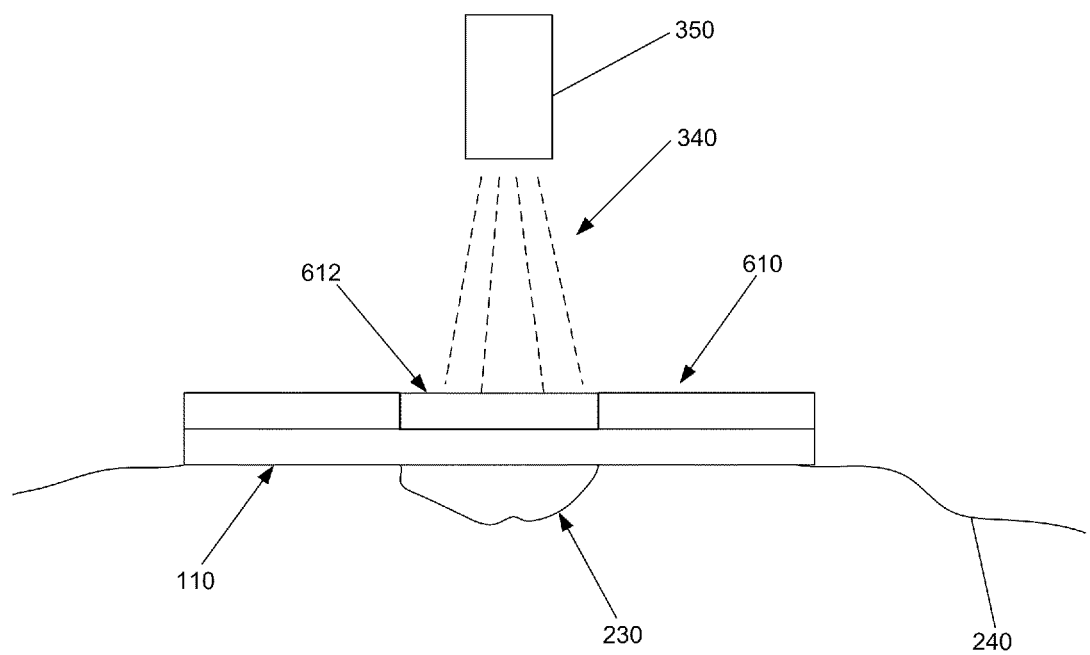
FIG. 6 illustrates exposure of the layer in which the light source passes through an opening created within the layer consistent with an additional aspect of the present disclosure.

Alternatively, as shown in FIG. 6, a suitable dye may be diffused into or impregnated within the collagen-flavin composite layer 110 to form dye regions 610, which may act to absorb light in the range of 360-375 nm or 440-480 nm. The regions may extend along the periphery of collagen layer 110 while leaving a portion of 612 of collagen-flavin composite layer 110 that does not contain dye. In this example, the composite layer may be exposed to light 340 from source 350 in a manner similar to that described above. In the example shown in FIG. 6, however, collagen-flavin composite layer 110 itself includes light blocking dye regions 610, so that mask 510 is unnecessary. Examples of light blocking dyes may include fluoroscein sodium, rose bengal and indocyanine green (ICG) that are commonly used as biologic dyes.

It is noted that instead of source 450, source 360 having envelope 320 may be used in conjunction with mask 410. In addition, mask 410 may be coextensive with envelope 320 in order to further minimize or eliminate exposure to portions of tissue 240 other than that affected by the lesion.

In one example, the collagen composite layer 110 includes a 1.0% riboflavin concentration, and the exposure time of photoradiation beam 340 is for approximately 3 to 15 minutes, depending on the size of the lesion. The exposure time may also be for duration of 5 minutes to one hour, and the intensity of light 340 may be within a range of 0.1 W/cm$^2$ to 2 W/cm$^2$. In addition, lesion or wound 230 is preferably maintained in a fixed position during the exposure, and radiation beam 340 may be in the form of collimated beam.

As discussed above, collagen-flavin composite layer 110 applied to a lesion or wound 230 may include riboflavin. However, as further noted above, it is also contemplated that collagen-flavin composite layer 110 may include lumichrome instead. Alternatively, collagen-flavin composite layer 110 may include lumiflavin. In a further example, collagen-flavin composite layer 110 may be preexposed to include preactivated riboflavin, which has been exposed to ultraviolet light having a wavelength in a range of 360-375 nm or blue light having a wavelength in the range of 440-480 nm prior to application to the lesion or wound 230. In addition, the collagen-flavin composite layer 110 may be applied to the lesion or wound 230 in a manner similar to that discussed above in reference to FIG. 2. Moreover, the same or similar exposure parameters (intensity, wavelength, and exposure duration) may also be employed and the sources discussed above in regard to FIGS. 2-4 may be used.

Collagen-flavin composite layer 110 adheres to the lesion or wound 230, covering and protecting the wound but over time may be dissolved by fluids naturally present in and/or human tissue surrounding the wound. In particular, depending on the concentration of collagen in collagen-flavin composite layer 110, the amount of time required for collagen-flavin composite layer 110 to dissolve may vary from approximately 5 minutes to approximately 30 days. Thus, an advantage of collagen-flavin composite layer 110 is that it adheres to the tissue surface 240 for a time sufficient to perform the exposure discussed above, and, for example, seal and glue the tissue together, optionally participate in tissue remodeling, and thereafter, harmlessly dissolves. Typically, there is no need for a practitioner to remove composite layer 110 once it is applied.

In another aspect of the present disclosure, membranes, scaffolds or patches of various kinds including, for example, the composition discussed above, can be glued over tissue defects. In this case, the membrane, scaffold or patch may be prebonded by overlaying the composition onto the respective surface. The composite may then be exposed to ultraviolet light having a wavelength in a range of 360-375 nm or blue light having a wavelength in the range of 440-480 nm to crosslink the composition to a membrane, scaffold or patch. A separate and nonexposed section of the composition may be placed on the tissue defect followed by the placement of the prebonded membrane, scaffold or patch in which the prebonded side is placed immediately adjacent to the nonexposed sections of the composition forming a sandwich configuration that is covering the tissue defect. The sandwich configuration may then exposed to ultraviolet light having a wavelength in a range of 360-375 nm or blue light having a wavelength in the range of 440-480 nm, resulting in sealing and closing the tissue defect by the photo-degradation of the chromophore present in composition, such as riboflavin. As a result, a reactive oxygen species (ROS) may be generated that may disrupt the three-dimensional structure of collagen fibers found in tissues as well as in the derivatized collagen (flavin carrier). Such disruption may promote crosslinking between tissue and the composition, thereby improving both adhesive and cohesive strength.

Figure 7A:
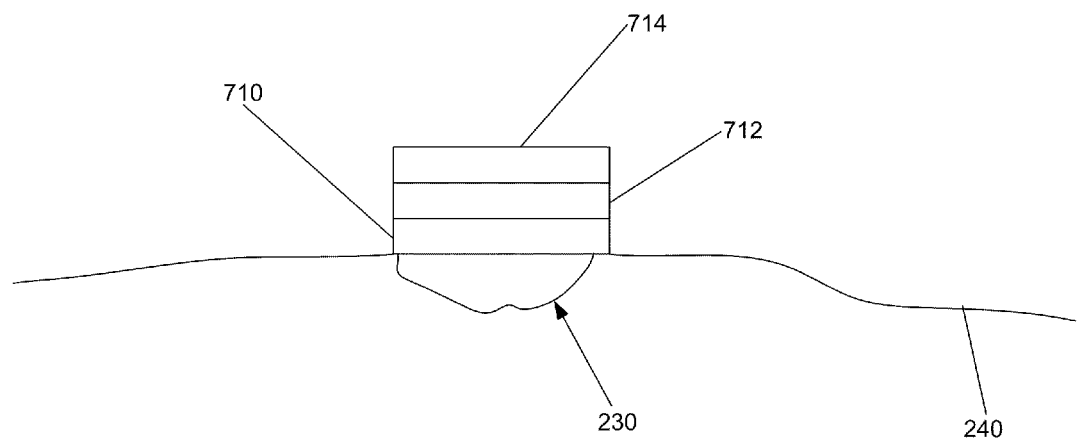
FIGS. 7a and 7b illustrate edge and perspective views, respectively, of a multilayered composition consistent with an additional aspect of the present disclosure.
Figure 7B:
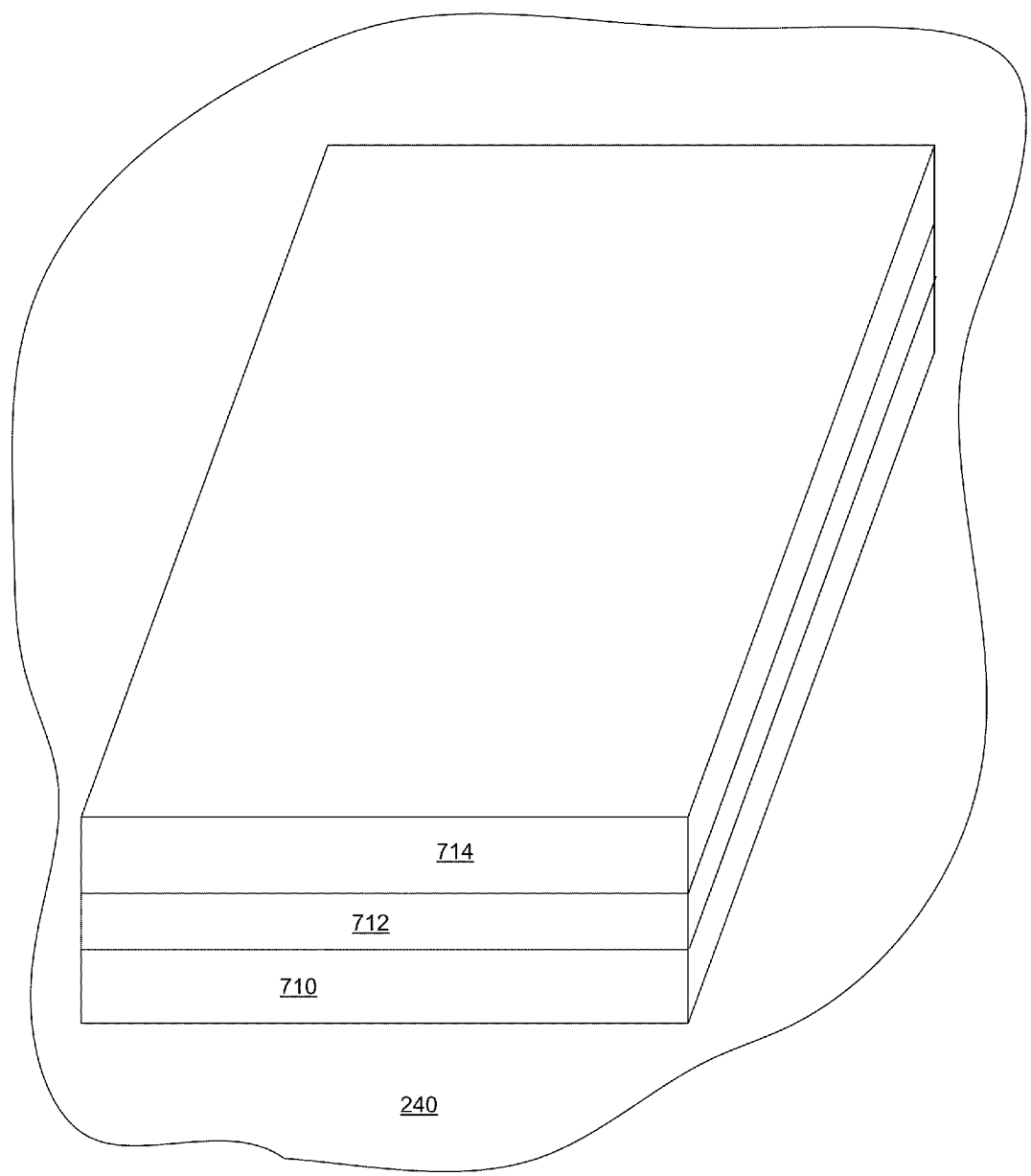

FIG. 7a illustrates an example of a multilayered structure 700 including a pre-exposed layer or composition 712 (e.g., exposed to light having a wavelength in a range of 360 nm-375 nm or in the range of 440 nm-480 nm for a duration of 1-5 minutes, for example) that has been bonded to a scaffold, membrane, or patch 714. Multilayer structure 700 further includes layer or composition 714, which may be similar to composition 712. As noted above, the pre-exposed layer 712 and patch 714, for example, may first be attached to each other. Thereafter, layer 712 may be attached to layer 710 to provide a sandwich structure, with layer 712 between layer 710 and patch 714. The sandwich structure may be further exposed to the wavelength noted above for 1-5 minutes, for example.

Layer 712 may include a composition similar to or the same as that noted above. In particular, layer 712 may include collagen, wherein a concentration of the collagen in layer is 712 is 100 mg/ml (10%) up to and including 600 mg/ml (60%). Layer 712 may also include a chromophore that produces reactive oxygen species upon exposure to electromagnetic radiation, such as light having a wavelength in a range of 360-375 nm or 440-480 nm. Layer 712, as further noted above, may be pre-exposed to such light for 1-5 minutes, for example.

Layer 710 may also include collagen, wherein a concentration of such collagen in layer 710 is 100 mg/ml (10%) up to and including 600 mg/ml (60%). Layer 710 may also include a chromophore that produces a reactive oxygen species upon exposure to electromagnetic radiation, such as light having a wavelength in one of the ranges of 360-375 nm or 440-480 nm. Layers 712 and 710 may include the same chromophore, such as riboflavin, lumiflavin or lumichrome. Alternatively, the chromophore in layer 710 may be different than the chromophore layer 712. In addition, the collagen in layers 712 and 714 may be derivatized with a $COO^-$ functional group, as discussed above.

Antimicrobial properties of the above-described exposed collagen layer with an incorporated chromophore may result from release of oxygen free radicals in combination with the generation of nucleotides that preferentially interrupt the rna or dna of pathogens that cause the infection. Accordingly, the above-described composition may be effective in a broad spectrum of pathogens, including bacteria, viruses, parasites and fungi. Due to the mechanism of action, development of resistance is unlikely. In addition, it has been observed that wound contamination has been significantly reduced after a single treatment, as discussed in the following example.

The following experiment demonstrates the effectiveness of compositions consistent with the present disclosure in sealing and antimicrobial applications. Here, a glue consistent with the present disclosure was used to seal a corneal incision (wound), and bursting pressures were measured after wound closure, as discussed in greater detail below.

A 2.85 mm keratome knife was used to create a non-self-sealing central perpendicular corneal wound (CPCW) in 15 cadaver calf eyes. Immediately after incisions were made, a digital manometer connected to the anterior chamber was zeroed. Wounds were then sealed with a novel biological solder consisting of a collagen-flavin composite. For this example the collagen concentration was 5% and the riboflavin 5%. A portable blue laser light was then used to activate the collagen-RB composite, resulting in cross-linking to tissue. After 3 minutes, wound stability was tested using a stepwise infusion of basic salt solution, and pressure changes were monitored. Bursting pressure was recorded.

A total of 15 fresh calf cadaver eyes were used, but only 13 eyes with bursting pressures below 1000 mm Hg (the maximum limit for the digital manometer) were included for analysis. The mean leaking IOP immediately after the CPCW in the non-sealed eyes was 88.00 mm Hg (SD 21.07). The mean bursting IOP after wound closure with the collagen-riboflavin composite glue was 339.07 mm Hg (SD 96.04).

The tested laser-activated solder was effective in sealing central full-thickness corneal wounds in cadaver calf eyes.

Advantages of compositions consistent with the present disclosure include elimination of dead spaces in wounds, thereby reducing the need for drains. In addition, compositions disclosed herein may bond to wound collagen, thereby aiding in the apposition of the wound surfaces and minimizing seroma (fluid) accumulation. Moreover, compositions consistent with the present disclosure may be provide a moist environment about the wound that encourages healing.

In addition, as described below, tensile tests were performed on tissue bonded or attached to a composition consistent with the present disclosure. The tensile tests were performed with a Mark-10G ESM force measurement stand, a FGV-5 digital force gauge and a set of Mark-10 G1008 grips for holding tissue which had been bonded or attached to a composition consistent with the present disclosure. All measurements were made at room temperature. For testing, the head drive of the force measurement stand was set for 1"/min at constant velocity as the load was increased. The force gauge in the tensile mode reads peak force with 1 gm resolution and ±1 gm accuracy. The samples were mounted between screw clamps that are designed with serrated interlocking jaws for securely holding the tissue, and pulled at constant velocity as the load was increased. As the soldered joint between the tissue and composition is pulled, the load cell of the force gauge measures the reaction force. The peak force corresponds to the breaking strength. The glued area is measured with a digital caliper, and the strength of the repair is quantified by comparing tensile strength values of each formulation. The failure mechanism is determined by visually inspecting the type of break. A cohesive failure is defined as a fracture at the incision line, but the adhesive remains attached to the tissue. An adhesive failure occurs with the material is detached from one side of the incision.

Figure 8:
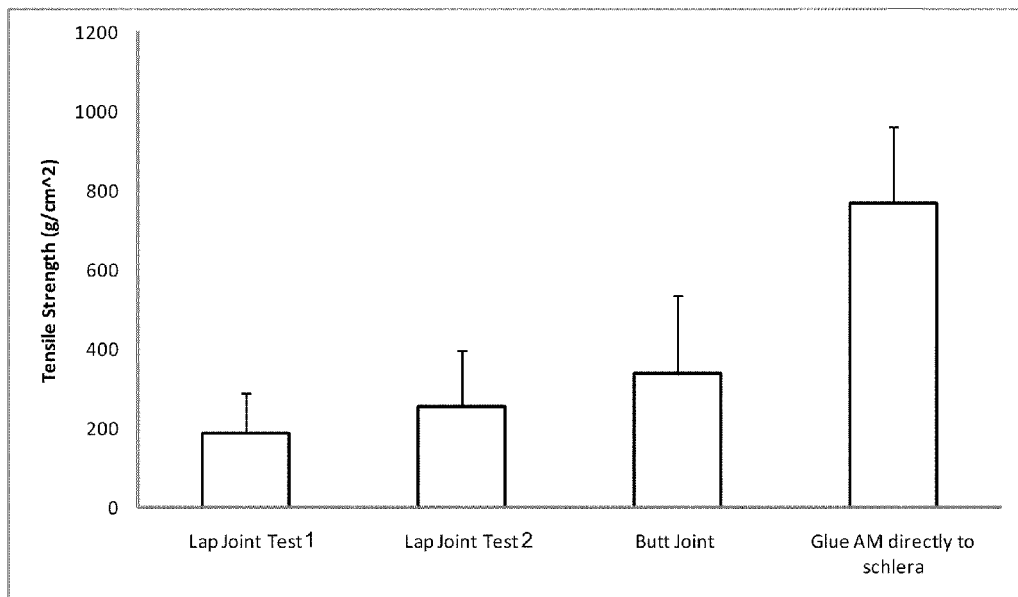
FIG. 8 illustrates various test results indicative of an advantage of a composition consistent with the present disclosure.

The average tensile strengths of compositions consistent with the present disclosure, as measured in different tensile tests, are shown in FIG. 8. Namely, in Lap Joint Test involved, the sample or test configuration included a sandwich of sclera tissue/composition/sclera tissue in which the composition or glue is between the overlapping sclera strips. Pulling force is on the opposing sclera strips. In Lap Joint Test 2, the sample or test configuration included sclera tissue that was bonded or attached to a composition consistent with the present disclosure to form an overlapping joint. Pulling force is on the composition in one direction and sclera in the opposite direction. In the Butt Joint Test, two strips of sclera were in the same plane with ends touching each other and the composition was placed on the joint to make a bridge over the two touching sclera ends. The pulling force was on the opposing sclera strips.

In the "Glue AM directly to sclera" test, an amniotic membrane (AM) was attached directly to the sclera by the composition or glue. Pulling force was on the amniotic membrane in an upward direction and holding the eye in a downward direction. The results shown in FIG. 8 illustrate relatively high tensile strengths of compositions consistent with the present disclosure and demonstrate that compositions consistent with the present disclosure are adequate for use as an adhesive for gluing tissue.

Figure 9A:
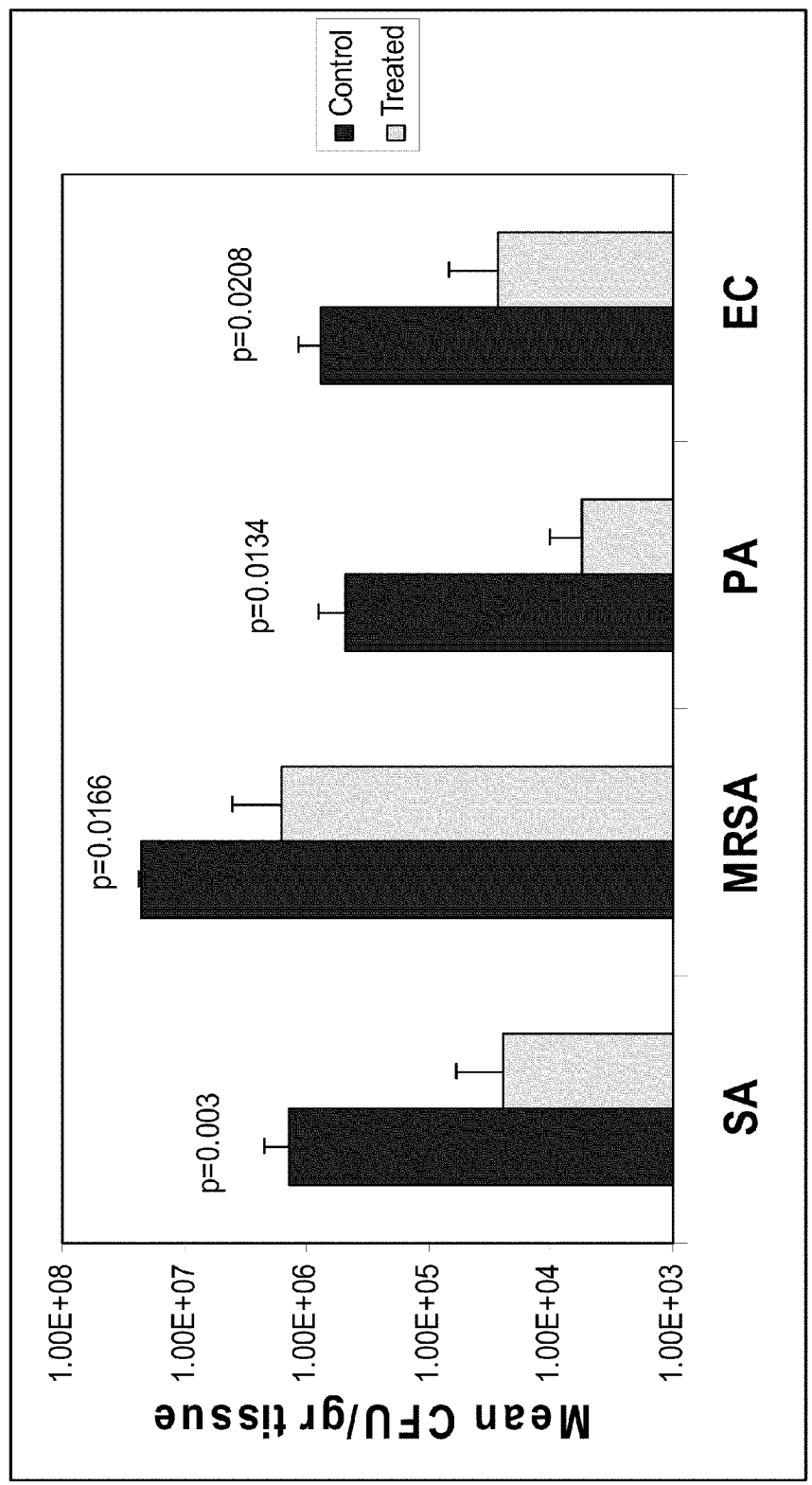

An acute infection model was created to investigate the potential for wound decontamination. Female retired breeder BALB/C mice (n=120, Jackson Labs) were anesthetized with IP Xylazine and Pentobarbital. Axially oriented 1 cm incisions were made on the dorsal midline after shaving, depilating with Nair® and cleaning the skin with 70% ethanol. *S. aureus*, MRSA, *E. coli* or *P. aeruginosa* were placed in the wounds by instilling 0.10 ml suspensions containing McFarland Unity densities ranging between $10^3$-$10^8$ CFU/ml. The animals were allowed to absorb the fluid for 10 minutes. Treated group animals received 1 cm×1 cm Riboflavin-5-phosphate/collagen composite wafer implants including compositions consistent with the present disclosure. The wounds were irradiated at 457 nm (300-500 mW output, 1 cm spot diameter) for 15 min using a diode pumped solid state laser (DPSSL) 10 min after implant insertion. The incisions were closed with polypropylene sutures and the animals were recovered and individually caged. Control group animals were handled similarly but did not receive the implant or photoradiation. Animals were euthanized at 24 hr post therapy with Xylazine and Pentobarbital overdose. Quantitative wound bacterial counts (Colony Forming Unit-CFU/g tissue) were determined using standard microbiological methods to measure bactericidal efficiency. The results of the above experiment are shown in the FIGS. 9a-9c. FIG. 9c demonstrates that the bactericidal effect, as measured by culture of wound fluid at time of sacrifice, increases with increasing irradiance or exposure of the compositions consistent with the present disclosure.

Photoirradiation of collagen-riboflavin 5 phosphate composites at 457 nm demonstrated a bactericidal effect on all tested bacterial strains in both the abscess and acute infection models in vivo, confirming observations that were made in vitro. This effect increased with increasing durations of photoradiation or exposure of the compositions consistent with the present disclosure, being most pronounced at 400 mW in all groups. Reductions of bacterial loads was typically 2-3 logs in both models at the parameters tested.

Figure 9B:
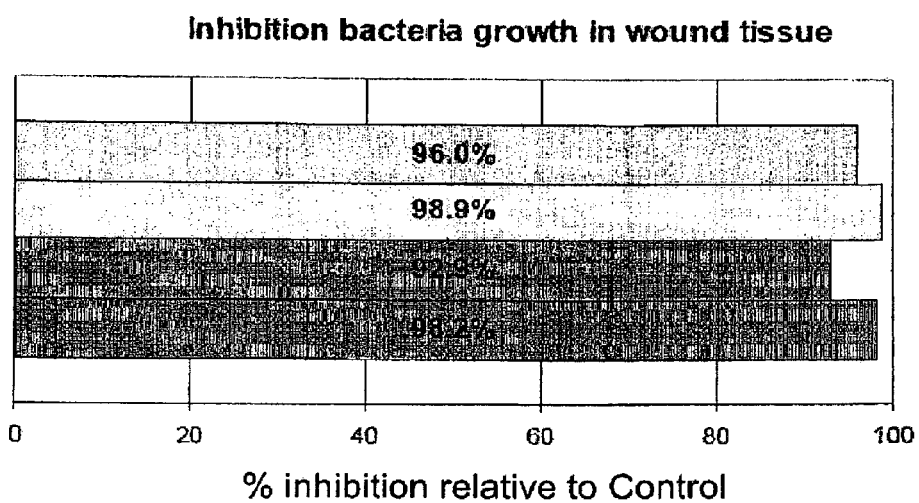

The results shown in FIGS. 9a-9c will next be described in greater detail. As noted above, these results were obtain in experiments in which compositions consistent with the present disclosure were exposed to light having a wavelength of 450 nm for 15 minutes. As shown in FIG. 9a, bacterial loads (in units of FCU/gram of tissue) were reduced approximately 2-3 log's for Staphylococcus aureus (SA), Methicillin-resistant Staphylococcus aureus (MRSA), Pseudomonas aeruginosa (PA) and Escherichia coli (EC) compared to the controls. Figure 9b illustrates that the percent reduction in bacterial viability as compared to the control for all bacterial strains studied was over 98% in all cases. Figure 9c shows the effect of power of the light source used to expose the compositions consistent with the present disclosure in destroying pathogens as compared to the control. In this case the higher power (400 mW) was more effective.

Thus, the above-described compositions are relatively strong tissue adhesives and possess anti-microbial properties. Accordingly, compositions consistent with the present disclosure are advantageous over conventional tissue adhesives and sealants.

Other embodiments will be apparent to those skilled in the art from consideration of the specification and practice of the subject matter disclosed herein. It is intended that the specification and examples be considered as exemplary only, with a true scope and spirit of the invention being indicated by the following claims.

What is claimed is:

1. A composition, comprising:
   collagen, wherein the concentration of the collagen in the composition is from 300 mg/ml up to and including 800 mg/ml, and wherein the collagen being derivatized with a $COO^-$ functional group; and
   riboflavin, wherein the concentration of the riboflavin is substantially equal to 1.0% (w/v) to 2.0% (w/v).

2. A composition in accordance with claim 1, wherein the concentration of the riboflavin in the composition is substantially equal to 1.0% (w/v).

3. A composition, comprising:
   collagen, wherein the concentration of the collagen in the composition is from 300 mg/ml up to and including 800 mg/ml; and
   a chromophore that produces a reactive oxygen species upon exposure to electromagnetic radiation, wherein the concentration of the chromophore is substantially equal to 1.0% (w/v) to 2.0% (w/v), and wherein the chromophore is selected from the croup consisting of: riboflavin, luminflavin, and lumichrome.

4. A composition in accordance with claim 3, wherein the chromophore includes riboflavin.

5. A composition in accordance with claim 3, wherein the concentration of the riboflavin in the composition is substantially equal to 1.0% (w/v).

6. A composition in accordance with claim 3, wherein the chromophore is lumiflavin.

7. A composition in accordance with claim 3, wherein the chromophore is lumichrome.

8. A composition in accordance with claim 3, wherein the collagen is gelatinized.

9. A composition in accordance with claim 3, wherein at least a portion of the collagen is derivatized with a $COO^-$ functional group.

10. A composition in accordance with claim 3, wherein the electromagnetic radiation has a wavelength in a range of 360 nm to 375 nm.

11. A composition in accordance with claim 3, wherein the electromagnetic radiation has a wave length in a range of 440 nm to 480 nm.

12. A composition in accordance with claim 11, wherein the wavelength is substantially equal to 450 nm.

13. A composition in accordance with claim 1, wherein the concentration of the collagen in the composition is from 300 mg/ml up to and including 600 mg/ml, the collagen being derivatized with a $COO^-$ functional group.

14. A composition in accordance with claim 3, wherein the concentration of the collagen in the composition is from 300 mg/ml up to and including 600 mg/ml, the collagen being derivatized with a $COO^-$ functional group.

15. A method, comprising:
    applying a composition in accordance with claim 4 to a tissue; and
    exposing the composition to optical energy having a wavelength in a range of 440-480 nm.

16. A method in accordance with claim 15, wherein the chromophore is riboflavin.

17. A method in accordance with claim 15, wherein the concentration of the riboflavin in the composition is substantially equal to 1.0% (w/v).

18. A method in accordance with claim 15, wherein the chromophore is lumiflavin.

19. A method in accordance with claim 15, wherein the chromophore is lumichrome.

20. A method in accordance with claim 15, wherein the collagen is gelatinized.

21. A method in accordance with claim 15, wherein at least a portion of the collagen is derivatized with a $COO^-$ functional group.

22. A method in accordance with claim 15, wherein the wavelength is substantially equal to 450 nm.

23. A method in accordance with claim 15, wherein an intensity of the optical energy in the collagen layer is in a range of 0.1 $W/cm^2$-2.0 $W/cm^2$.

24. A method in accordance with claim 15, wherein the tissue includes a human tissue lesion or wound.

25. A method in accordance with claim 15, wherein said exposure is for a duration of 5 min-30 min.

26. A composition comprising:
    a first layer including:
    a first collagen, wherein the concentration of the first collagen in the first layer is from 300 mg/ml up to and including 800 mg/ml, and
    a first chromophore that produces a reactive oxygen species upon exposure to electromagnetic radiation, the first layer having been exposed to electromagnetic radiation having a wavelength in a range of 350-375 nm or 440-489 nm, wherein the concentration of the first chromophore is substantially equal to 1.0% (w/v) to 2.0% (w/v), and wherein the first chromophore is selected from the group consisting of: riboflavin, luminflavin, and lumichrome; and
    a second layer including:

a second collagen, wherein the concentration of the second collagen in the second layer is from 300 mg/ml up to and including 800 mg/ml, and a second chromophore that produces a reactive oxygen species upon exposure to electromagnetic radiation.

27. A composition in accordance with claim 26, wherein the first and second chromophore is riboflavin.

28. A composition in accordance with claim 26, wherein the first and second chromophore is lumiflavin.

29. A composition in accordance with claim 26, wherein the first and second chromophore is lumichrome.

30. A composition in accordance with claim 26, wherein the first and second collagen is derivatized with a $COO^-$ functional group.

* * * * *